(12) United States Patent
Cheetham

(10) Patent No.: US 8,336,390 B2
(45) Date of Patent: Dec. 25, 2012

(54) APPARATUS AND METHOD FOR DETERMINING THE TENSILE BOND STRENGTH OF A DENTAL MATERIAL

(75) Inventor: Joshua James Cheetham, Chicago, IL (US)

(73) Assignee: SDI Limited, Bayswater (AU)

(*) Notice: Subject to any disclaimer, the term of this patent is extended or adjusted under 35 U.S.C. 154(b) by 125 days.

(21) Appl. No.: 12/791,006

(22) Filed: Jun. 1, 2010

(65) Prior Publication Data

US 2010/0307259 A1 Dec. 9, 2010

(30) Foreign Application Priority Data

Jun. 3, 2009 (AU) .................................. 2009902544

(51) Int. Cl.
*G01N 3/08* (2006.01)
(52) U.S. Cl. .......................... 73/827; 73/150 A

(58) Field of Classification Search ................ 73/150 A, 73/826–827
See application file for complete search history.

(56) References Cited

U.S. PATENT DOCUMENTS

| | | | | |
|---|---|---|---|---|
| 4,552,706 A | * | 11/1985 | Ducote | 264/3.1 |
| 4,888,982 A | * | 12/1989 | Chilton et al. | 73/81 |
| 5,374,808 A | * | 12/1994 | Coultrip et al. | 219/633 |
| 5,649,447 A | * | 7/1997 | Van Avery | 73/150 A |
| 6,289,741 B1 | * | 9/2001 | Ghetzler et al. | 73/827 |

* cited by examiner

*Primary Examiner* — Max Noori
(74) *Attorney, Agent, or Firm* — William H. Holt

(57) ABSTRACT

An apparatus and method for determining the tensile strength of dental materials utilizing a mold. The dental material is placed in the mold and is adhered to a surface. The mold containing the dental material is then engaged with a pulling device which subjects the mold to a measured force to disengage the dental material from the surface. This provides a measure of the tensile strength of the dental material.

8 Claims, 4 Drawing Sheets

APPARATUS AND METHOD FOR DETERMINING THE TENSILE BOND STRENGTH OF A DENTAL MATERIAL

FIELD OF THE INVENTION

The present invention relates to an apparatus and method for determining the tensile bond strength of a dental material.

SUMMARY OF THE INVENTION

In accordance with one aspect of the present invention there is provided an apparatus for determining the tensile bond strength of a dental material which comprises a mould arranged to receive a quantity of material to be tested, pulling means for engaging with the mould and means for applying a force to the pulling means when engaged with the mould to disengage the mould from a bonding surface to which material in the mould is adhered.

In accordance with a further aspect of the present invention there is provided a method of determining the tensile bond strength of a dental material, which comprises placing the material in a mould and adhering the material in the mould to a bonding surface, engaging the mould with a pulling means, exerting a measured force on the pulling means so as to cause the mould to be disengaged from the bonding surface such that the tensile bond strength of the material can be determined.

DESCRIPTION OF THE DRAWINGS

The present invention will now be described, by way of example, with reference to the accompanying drawings, in which.

DETAILED DESCRIPTION OF THE INVENTION

Figure 1:
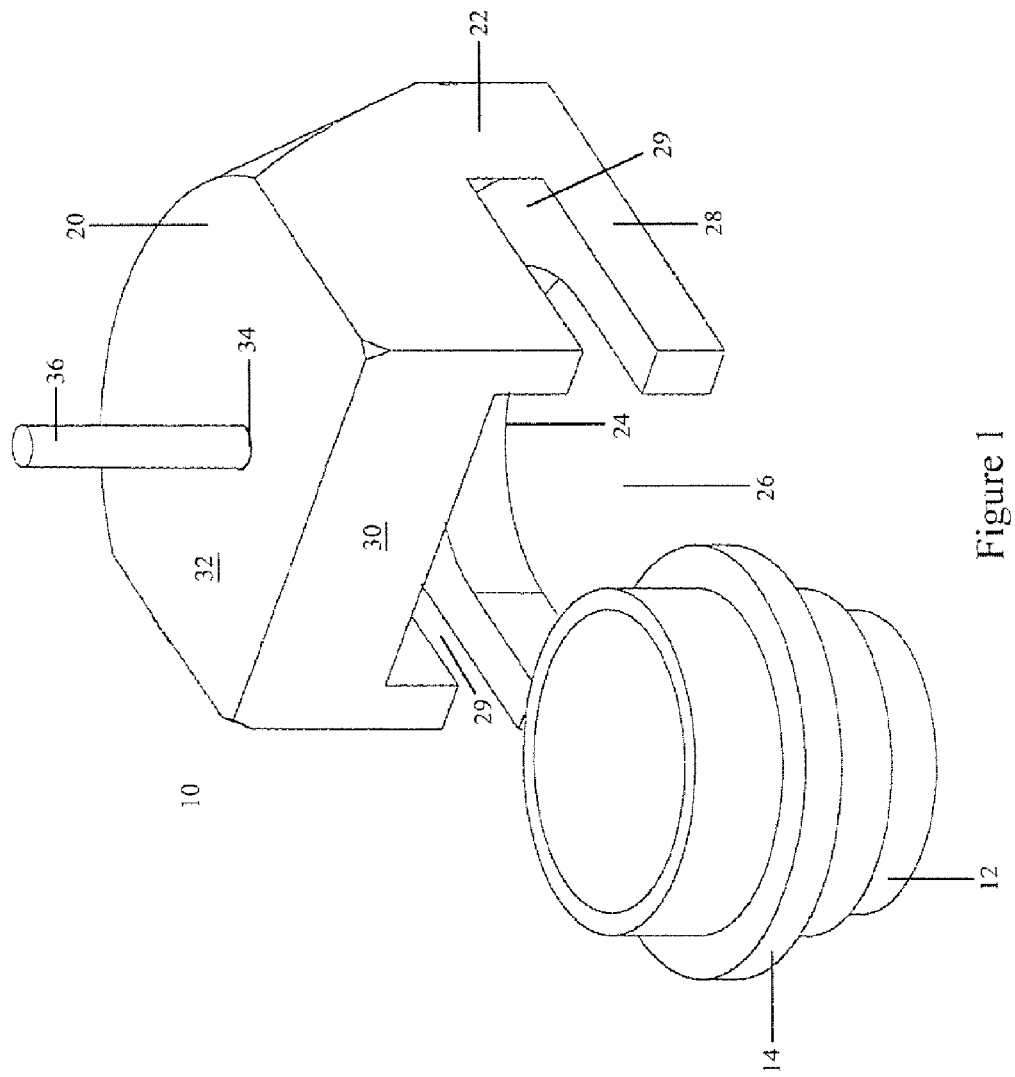
FIG. 1 is a perspective view of an apparatus of the present invention showing a mould puller apparatus and a first embodiment of mould in separated condition.
Figure 2:
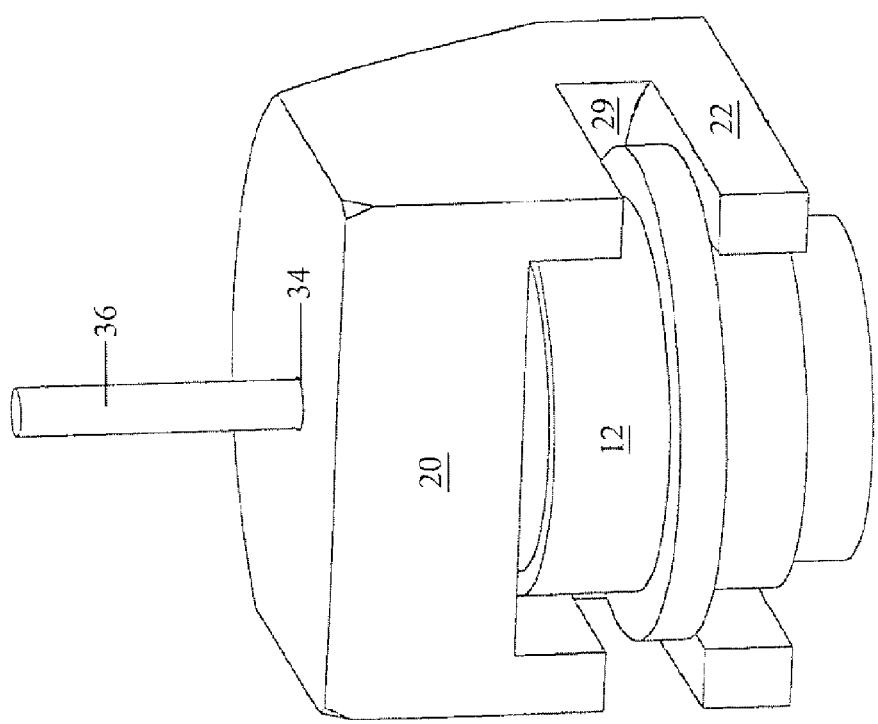
FIG. 2 shows the apparatus of FIG. 1 with the mould puller apparatus and the mould in engaged condition.
Figure 3:
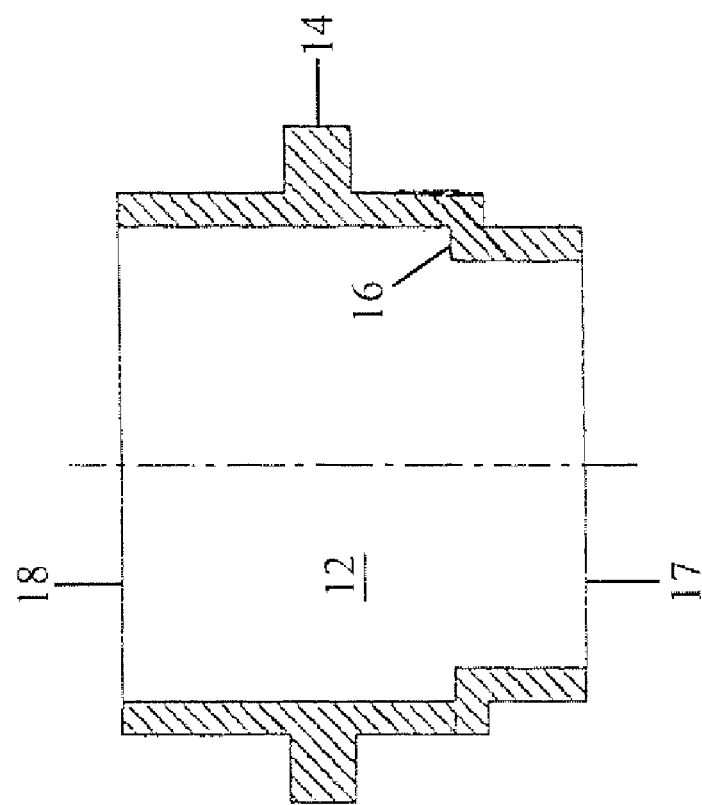
FIG. 3 is a vertical cross-sectional view of the mould of FIGS. 1 and 2.

In FIGS. 1 to 3 of the accompanying drawings there is shown an apparatus 10 for determining the tensile bond strength of a material such as a dental composite material.

The apparatus 10 comprises a hollow mould 12 which is provided with an external flange 14 which extends circumferentially laterally around the mould 12. Further, as shown in FIG. 3 the mould 12 has an internal step 16 at an intermediate level of an interior of the mould 12. Further the mould 12 has open ends 17 and 18 as shown in FIG. 3.

The apparatus 10 also comprises a mould puller 20 which comprises a lower portion 22 which is provided with an opensided recess 24 having an entrance portion 26 on one side.

The mould puller 20 also has an upper portion 30. Further, the lower portion 22 is also provided with opposed arms 28 which extend outwardly on respective sides of the recess 24. Further, the arms 28 the define gaps 29 between the upper portion 30 and the lower portion 22. The gaps 29 are arranged to receive the flange 14 of the mould 12 when the latter is inserted in the recess 24.

The upper portion 30 has an upper surface 32. The upper surface 32 is provided with a centrally disposed hole 34. A flexible cable 36 is anchored in the hole 34 by any suitable means.

In use, the mould 12 is held against a bonding surface (not shown) by any suitable means such as a rig comprising a spring biased pressure plate. The bonding surface may be precoated with a dental adhesive. The mould 12 is then filled whilst being held in contact with the bonding surface with a material to be tested such as a dental composite material. The material is allowed to cure in known manner and adheres to the bonding surface.

After the material is cured, the mould puller 20 is placed over the mould. This is done by engagement of the gaps 29 with the flange 14 as shown in FIG. 2.

The cable 36 is attached to a tensile compression testing machine (as shown). A measured pulling force is applied to the cable 36 which causes the mould 12 to be disengaged from the bonding surface. The force required to achieve this result is recorded and provides a measure of the tensile bond strength of the cured dental composite material.

The presence of the internal step 16 ensures that the mould 12 and the entire charge of dental material is removed from the bonding surface by the tensile compression testing machine The mould 10 of FIGS. 1 to 3 is particularly envisaged for use in determination of micro tensile bond strength such as of a sample having a cross sectional bonding area of about 1 mm square. In this connection the mould 10 typically has an internal dimension in the range from 0.5 to 3 mm at a lower end thereof as seen in FIG. 3.

Figure 4:
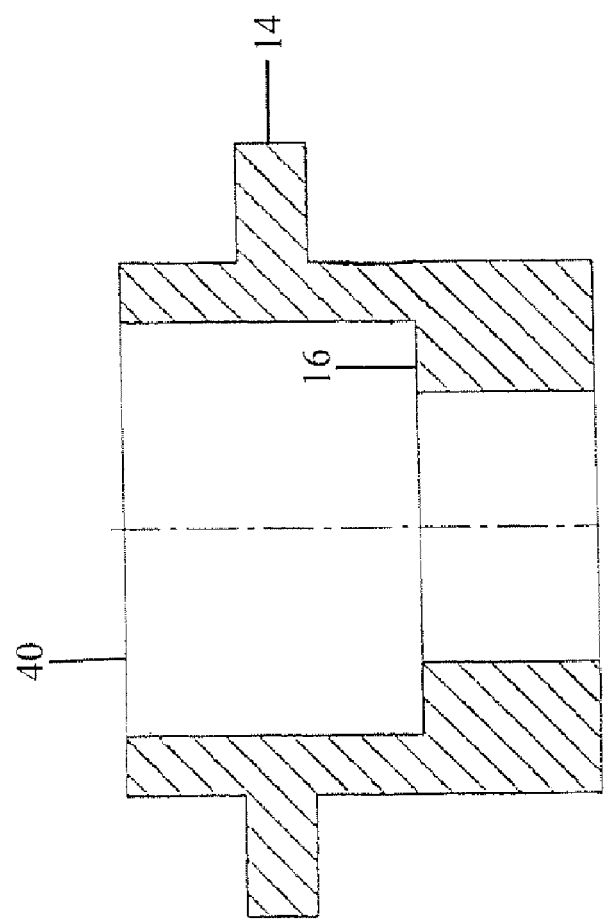
FIG. 4 is a vertical cross-sectional view of a second embodiment of mould of the present invention.

The mould 40 of FIG. 4 is particularly envisaged for use in determination of micro tensile bond strength of a smaller area. In this connection the mould 40 typically has an internal dimension in the range from 0.5 to 1.5 mm at a lower end thereof as seen in FIG. 4.

Modifications and variations as would be apparent to a skilled addressee are deemed to be within the scope of the present invention.

The invention claimed is:

1. A combination of a mould and a mould puller for determining the tensile bond strength of a moldable material, said mould including an external flange extending at least partially about an outer surface of said mould, said mould including a hollow interior for receiving said moldable material and an open bottom for permitting said moldable material to contact with an underlying bonding surface while being cured within said mould; said mould puller including means for engaging with said flange, pulling means carried by said mould puller for attaching said mould puller to a tensile testing machine for applying a measured pulling force to said mould for disengaging said moldable material from said bonding surface and recording the tensile force required for disengaging said moldable material from said bonding surface.

2. The combination as defined in claim 1 wherein said mould has an open top portion for receiving said moldable material.

3. The combination as defined in claim 2 wherein said moldable material is a dental material comprised of a dental composite resin.

4. The combination as defined in claim 1 wherein said means for engaging with said flange include a pair of spaced arms for underlying said flange on opposite sides of said mould, whereby lifting of said arms by said pulling means disengages said molding material from said bonding surface.

5. The combination as defined in claim 1 wherein said pulling force raises said mould from said bonding surface, and said moldable material remains within said mold.

6. The combination as defined in claim 5 wherein said mould includes an internal step at an intermediate level of the interior of said mould for ensuring that said mould and all of said moldable material are removed from said bonding surface.

7. A method of determining the tensile bond strength of a moldable material, said method including the steps of inserting moldable material in a mould having an open end, exposing a portion of said moldable material at said open end, engaging and adhering said portion of moldable material with a bonding surface, curing said moldable material, and exerting a measured pulling force on said mould for disengaging said moldable material from said bonding surface whereby the tensile bond strength of said moldable material is determined.

8. The method as defined in claim 7 including the step of selecting said moldable material to be a dental material comprising a dental composite resin, and allowing said resin to cure while in contact with said bonding surface.

* * * * *